US006334995B1

(12) United States Patent
Chatterjee et al.

(10) Patent No.: US 6,334,995 B1
(45) Date of Patent: *Jan. 1, 2002

(54) PROCESS FOR THE PREPARATION OF TECHNETIUM-99M DIETHYLENE TRIAMINE PENTA-ACETIC ACID DIESTER

(75) Inventors: Mita Chatterjee; Karabi Sen; Some Nath Banerjee, all of Calcutta (IN)

(73) Assignee: Council of Scientific & Industrial Research, New Delhi (IN)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/046,754

(22) Filed: Mar. 24, 1998

(51) Int. Cl.$^7$ .................... A61K 51/00; A61M 36/14
(52) U.S. Cl. .................... 424/1.65; 534/14; 206/223; 424/1.11; 424/9.1
(58) Field of Search .............. 424/1.11, 1.65, 424/9.1, 9.3, 9.4, 9.5, 9.6, 9.7; 534/7, 10–16; 562/607; 206/569, 570, 223

(56) References Cited

U.S. PATENT DOCUMENTS

| 5,275,801 A | * | 1/1994 | Niedballa et al. | 424/1.65 |
| 5,676,923 A | * | 10/1997 | Platzek et al. | 424/1.11 |
| 5,808,091 A | * | 9/1998 | Linder et al. | 548/341.1 |
| 5,859,214 A | * | 1/1999 | Gries et al. | 534/16 |
| 6,027,710 A | * | 2/2000 | Higashi et al. | 424/1.65 |

OTHER PUBLICATIONS

Dewanjee et al, vol. 132, p. 711–716, Pharmacodynamics of Stannous Chelates Administered with 99mTc–Labeled Chelates, 1979.*

* cited by examiner

*Primary Examiner*—Dameron L. Jones
(74) *Attorney, Agent, or Firm*—Rines and Rines

(57) ABSTRACT

A technetium-99m radiolabelled diethylene triamine pentaacetic acid diester kit and process for its preparation for the diagnosis of renal disorders wherein technetium-99m diethylene triamine pentaacetic acid dimethyl ester has Rf value= zero in silica gel/acetone TLC system and Rf value=1 in silica gel/acetonitrile water (1:1) TLC system and technicium-99m diethylene triamine pentaacetic acid dimethyl ester movement is of the order of half of the distance as compared to the standard compound, Technicium-99m dithelene triamine pentaacetic acid, on conducing paper electrophresis.

22 Claims, 2 Drawing Sheets

Scintiphoto of Dog after I.V. injection of [1] 99mTc-DMDTPA; [2] 99mTc-MAG₃ at (1A & 2A) 5 min., (1B & 2B) 10 min., (1C & 2C) 20 min., (1D & 2D) 30 min., and AREA OF INTEREST ANALYSIS on kidneys during the same experiment.

PROCESS FOR THE PREPARATION OF TECHNETIUM-99M DIETHYLENE TRIAMINE PENTA-ACETIC ACID DIESTER

FIELD OF INVENTION

The present invention to a technetium-99m radiolabelled diethylene triamine pentaacetic acid diester kit for the diagnosis of renal disorders.

BACKGROUND

For accurate evaluation of degree of renal disorder estimation rate of transfer of some specified substances such as technetium-99m diethylene triamine pentaacetic acid and iodine-131 orthoiodo-hippurate from blood to urine are to be determined. These compounds can be eliminated from blood either by glomerular filtration or by renal tubular secretion.

Technetium-99m diethylene triamine pentaacetic acid which is widely available and used for above said estimation, but since it is cleared by glomerular filtration, the extraction efficiency is only 20%. Therefore, while using this reagent, a low target to background ratio is produced and in many cases non-diagnostic images are obtained with patients having impaired renal function.

Orthoiodo-hippurate labeled either with iodine-131 or with iodine-123 which is also used for the above said estimation, is eliminated mainly by renal tubular secretion and therefore, has a very high extraction efficiency (87%). This compound is extremely useful for patients with poor renal function. However, iodine-131 not only impairs a high radiation dose to patients but shows a poor spatial resolution; this is due to its non-optimal energy characteristics. On the other hand, iodine-123 has an ideal energy but is very expensive and not available widely. These problems led to the search for an agent which will have similar renal property of orthoiodo-hippurate but labeled with a radionucleide of optimal energy characteristics such as technetium-99m.

After a decade of research in this area, a compound technetium-99m mercaptoacetylglycylglycylglycine was offered for clinical use. However, this compound deviated considerably from the nearly optimal renal properties of iodine-131 orthoiodo-hippurate in the following way:

1. Renal extraction of technetium-99m mercaptoacetylglycylglycylglycine was only 53% compared to that of iodine-131 orthoiodo-hippurate which was 79%.
2. High protein binding (77%) of technetium-99m mercaptoacetylglycylglycylglylcine compared to a moderate value (32%) of iodine-131 orthoiodo-hippurate.
3. Technetium-99m mercaptoacetylglycylglycylglycine is prohibitively expensive and not available in this country.
4. Technetium-99m mercaptoacetylglycylglycylglycine kit needs considerable skill to reconstitute or otherwise it may produce variable results.
5. Unwanted accumulation in hepatobiliary system is observed for technetium-99m mercaptoacetylglycylglycylglycine unlike that of iodine-13 1 orthoiodo-hippurate.

To solve these difficulties we developed a new compound, viz., technetium-99m diethylene triamine pentaacetic acid diester and a process for the preparation of this compound.

OBJECTS OF INVENTION

It is accordingly an object of the invention to provide such a new compound and process for its preparation that obviates such prior difficulties, and a novel diagnostic kit using such new compound.

SUMMARY OF INVENTION

Accordingly, the present invention provides a technetium-99m radiolabelled diethylene triamine pentaacetic acid diester kit for the diagnosis of renal disorders wherein technetium-99m diethylene triamine pentaacetic acid dimethyl ester has Rf value=zero in silica gel/acetone TLC Thin layer chromatography system and Rf value=1 in silica gel/acetonitrile water (1:1) TLC system and technicium-99m diethylene triamine pentaacetic acid dimethyl ester movement is of the order of half of the distance as compared to the standard compound, technicium-99m dithelene triamine pentaacetic acid, on conducting paper electrophoresis.

The invention further provides a process for the preparation of a technetium-99m radiolabelled diethylene triamine pentaacetic acid diester kit for the diagnosis of renal disorders which comprises:

(a) Adding appropriate amount of stannous ion to a dilute aqueous solution of diethylene triamine pentaacetic acid diester prepared by known methods
(b) Keeping the resultant solution obtained in step (a) in an evacuated rubber sealed injection vial flushed with nitrogen;
(c) lyophilizing the said kit and storing the lyophilized product as obtained in step (b) at 4° C.;
(d) radiolabelling the said lyophilised product obtained with Tc-99by allowing the kit to attain the room temperature before addition of 99m TcO$_4$
(e) shaking the kit vigorously to obtain the radiolabelled product available for use within a period of one hour.

In an embodiment of the invention, diethylene triamine pentaacetic acid diester used is prepared by

[a] esterifying dianhydride of diethylene triamine pentaacetic acid by conventional methods,
[b] evaporating the resulting semi-solid mass,
[c] titrating with an organic solvent to get the crude diester, and
[d] preparing the crude diester by recrystallisation from alcohol.

In another embodiment of the invention, esterification is effected by heating dianhydride of diethylene triamine pentaacetic acid with an alcohol in the presence of a solvent.

In a further embodiment of the present invention, the solvent used is selected from pyridine, piperidine, picoline and the like.

In yet another embodiment of the invention, the solvent used for tritration is selected from petroleum ether, benzene; toluene and the like.

In yet another modification of the present invention, the alcohol used for crystallization is selected from methanol, ethanol, propanol, isopropanol and the like. Further, in the preparation of the techetium-99m radiolabelled diethylene triamine pentaacetic acid diester kit for the diagnosis of renal disorders, stannousions are introduced by dissolving stannous chloride in dihydrate in HCI diluted nitrogen purged water.

BRIEF DESCRIPTION OF THE DRAWINGS

The invention will now be explained in connection with the accompanying drawings, FIGS. 1 and 2 of which present dog kidney serial images and corresponding time activity curves demonstrating clearance of radioactivity from the kidneys for a pair of injected preferred radiopharmaceuticals embodying the use of the novel compounds of the invention.

DETAILED DESCRIPTION OF THE INVENTION

Figure 1:
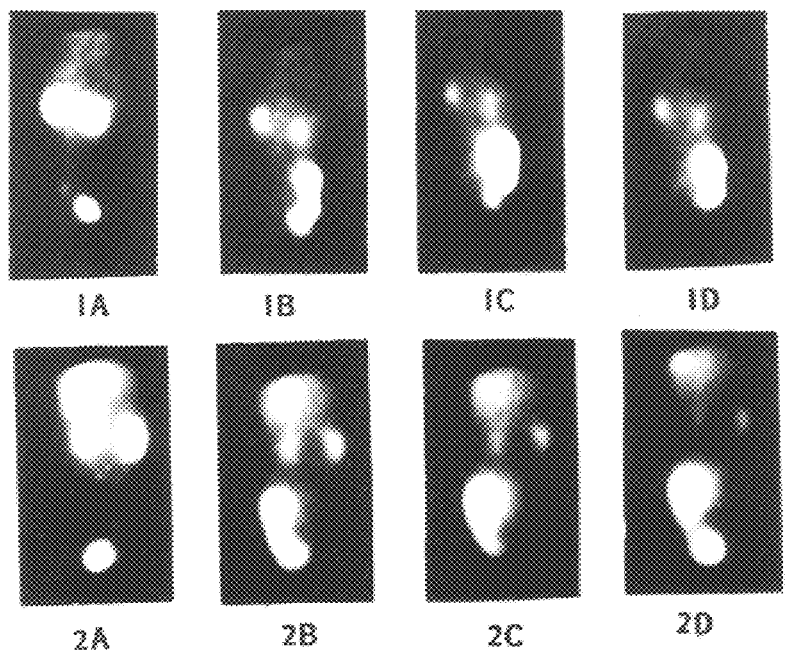
Figure 1:
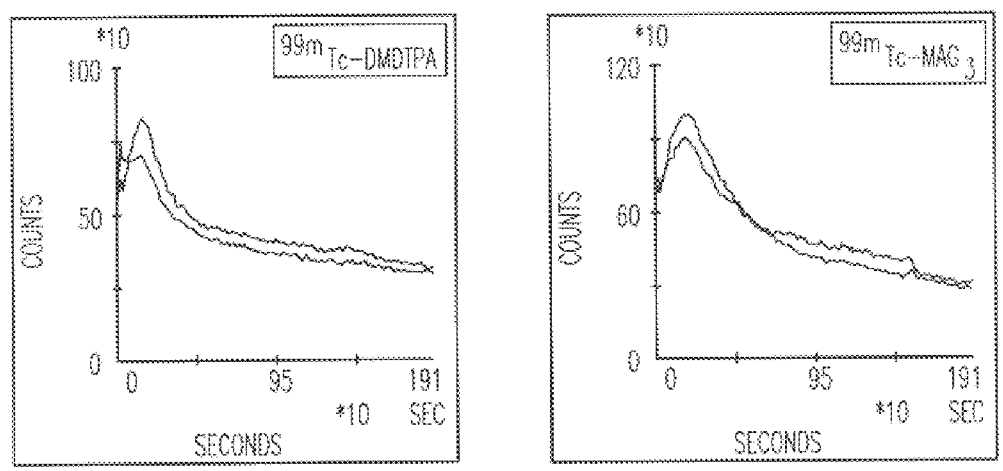

The invention will now be further described with reference to the details and the examples which should not be construed to limit the scope of the invention. Technetium 99m diethylene triamine pentaacetic acid diester is prepared by:

1. Esterification of the dianhydride of diethylene triamine pentaacetic acid.
2. formulation of frozen kit containing diethylene triamine pentaacetic acid dimethylester and stannous ion for easy radiolabeling, and
3. Radiolabeling of the above frozen kit with 99m $TcO_4$. Diethylene triamine pentaacetic acid dianhydride is prepared from diethylene triamine pentaacetic acid and acetic anhydride according to the procedure of W. C. Eckeliiian et al. (J. Pharm. Sci. 64, 704–706, 1975).

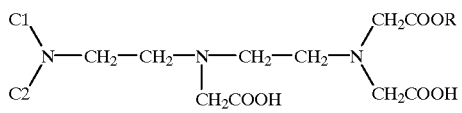

Diethylene Triamine Penaacetic Acid Diester

Diethylene triamine pentaacetic acid dianhydride was converted to dietilylene triamine pentaacetic acid diester by heating it with alcohol in presence of a solvent. Usually eighteen to twenty hours of reaction period is sufficient. The mixture was then evaporated and the semisolid mass was triturated with a solvent to furnish the crude diester. This was then purified by recrystallising from aqueous alcohol to furnish the desired material which was characterized by melting point determination, elemental analysis and proton magnetic resonance spectroscopy.

A kit for radiolabeling diethylene triamine pentaacetic acid diester was prepared from a dilute aqueous solution of the above ligand to which appropriate amount of stannous ion was added. The kits vials were then lyophilized and stored at 4° C. While radiolabeling with technetium-99m, the kit was allowed to attain room temperature and desired amount of aqueous 99m-$TcO_4$ was injected into the kit vial. The radiolabeled product thus obtained was characterised by thin layer chromatography and paper electrophoresis and was consumed in a short while.

An Example of the Process

[a] Preparation of diethylecue triamiliie peiitancetic acid dinicetihyl ester

To a solution of diethylene triamine pentaacetic acid dianhydride (7.2 g) in dry pyridine (120 ml) was added dry methanol (3 ml) and the mixture was heated under reflux for 18 hours. The material was then evaporated and the residual semisolid mass was triturated with diethyl ether to furnish solid crude ester (7 g). This was then purified by recrystallisation from ethanol-water (1:1) to furnish the pure material m.p. 176–178°. PMR ($D_2O$) δ 3.20–3.56 (br, 8H, >N—C$\underline{H}_2$—C$\underline{H}_2$—N—C$\underline{H}_2$—C$\underline{H}_2$—N<); 3.48 (S, 6H, 2×$CO_2C\underline{H}_3$); 3.94–4.28 (m, 1 OH, 3×C$\underline{H}_2CO_2H$ and 2×C$\underline{H}_2$—$CO_2CH_3$) Anal. calculated from $C_{16}H_{27}N_3O_{10}$. C, 45.60; H, 6.46; N, 9.97 found C, 45.34; H, 6.78; N, 9.76%).

[b] Kit formulation of diethylene triamixie pentaacetic acid dimetliyl ester for radiolabeling:

To evacuated rubber sealed injection vials flushed with nitrogen was added a solution of diethylene triamine pentaacetic acid dimethyl ester (10 mg) in water (1 ml) to which sodium hydroxide solution was added just to dissolve the material which was adjusted to pH 4 by hydrochloric acid and then stannous chloride solution (50 μl) was added which was prepared by dissolving stannous chloride dihydrate (10 mg) in hydrochloric acid (6N, 50 μl) diluted with $N_2$ purged water (10 ml) and the pH was readjusted to 4 and lyophilized.

[c] Technetium-99mi-radiolabeling of diethylene triamine pentaacetic acid dimethyl ester kit The kit as prepared above was allowed to attain room temperature and technetium-99m pertechnetate (99m $TcO_4$) (2.20 mCi in 0.1–0.2 ml of water) was added, shaken vigorously and used within an hour.

Complete Chemical and Biological Specification of Technetium-99m- dietllylelle triamine peiltaacetic acid dimethyl ester:

[a] Thin Layer Chromatography (TCL):

Two TLC systems were used (a) silica gel/acetone and silica gel/acetonitrile-water (1:1). In these two systems, technetium-99m diethylene triamine pentaacetic acid dimethyl ester showed Rf values of 0 and 1 respectively.

[b] Paper Electrophoresis:

This was conducted on Whatman paper strip (61 cm×26 cm) soaked in bicarbonate buffer (0.01 M, pH 7) on which technetium-99m-diethylene triamine pentaacetic acid dimethyl ester was spotted along with technetium-99m-diethylene triamine pentaacetic acid as standard. A potential difference of 3,000 volts was applied across the paper and the system was allowed to run for 60 min. Technetium-99diethylene triamine pentaacetic acid dimethyl ester moved 8 cm and the standard compound moved 16 cm, both towards anode under the above experimental condition.

Biological evaluation of technetium-99m diethylenie triamine pentaacetic acid diester by comparative biodistribution with iodine-131 orthoiodo-hippurate and technetium-99m mercaptoacetylglycylglycylglycine.

The comparative biodistribution experiment was undertaken in mice and rats. In mice either technetium-99m diethylene triamine pentaacetic acid diester or technetium-99m mercaptoacetylglycylglycylglycine were injected via the tail vein along with iodine-131 orthoiodo-hippurate. Rats were anaesthetised with urethane and the above radiochemicals were injected via the femoral vein. After predetermined time interval the animals were sacrificed and the organs were taken in the counting vial. Considerable care were exercised not to loose any urine during the process. The biodistribution results were summarised in Table 1.

Plasma Clearance

Renal plasma clearance of technetium-99m diethylene triamine pentaacetic acid dimethyl ester was studied in rats by single injection method. Two plasma samples were collected at 20 and 30 min time point. The clearance was calculated using a single compartment model. Iodine-131 orthoiodo-hippurate was coinjected as standard. This experiment was also performed with technetium-99m mercaptoacetylglycylglycylglycine. The clearance values were 1.39 and 1.45 ml/min 100 g for the above two compounds respectively and the value of iodine-131 orthoiodo-hippurate was 2.68 ml/min/100 g. The corresponding values in dog (10–12 kg) for technetiumn-99m diethylene triamine pentaacetic acid dimethyl ester and technetium-99m mercaptoacetylglycylglycylglycine along with coinjected hippurate were 72, 80 and 157 ml/min. These values are much higher than technetium-99m diethylene triamine pentaacetic acid in rats (0.82 ml/min 100 g) or dogs (43 ml/min).

pared to the tripeptide derivative mercaptoacetylglycylglycylglycine, therefore, making the former more affordable for clinical use. Again labeling of diester of diethylene triamine pentaacetic acid with technetium-99m is much simpler than mercaptoacetylglycylglycylglycine and is expected to produce a uniform labeled product easily like that of its precursor diethylene triamine pentaacetic acid. On the contrary, variation in biological results of technetiurn-99m mercaptoacetylglycylglycylglycine is well documented.

We claim:

1. A process for the preparation of a technetium-99m radiolabelled diethylene triamine pentaacetic acid diester kit for the diagnosis of renal disorders which comprises:

TABLE 1

Biodistribution of Iodine-131 orthoiodo-hippurate (I), Technetium-99m diester of diethylene-triamine pentaacetic acid (2), Technetium-99m marcaptoacetylglycylglycylglycine (3), Technetium-99m diethylene triamine pentaacetic acid (4) in rats and mice at 10 min and 30 min post-injection expressed as percent dose per organ

| | Blood | | Liver | | Intestine | | Kidney | | Urine | |
|---|---|---|---|---|---|---|---|---|---|---|
| | 10 min | 30 min | 10 min | 30 min | 10 min | 30 min | 10 min | 30 min | 10 min | 30 min |
| RAT | | | | | | | | | | |
| 1. | 5.61 ± 0.87 | 1.47 ± 0.28 | 3.29 ± 1.14 | 0.80 ± 0.12 | 2.12 ± 0.41 | 1.92 ± 0.39 | 3.72 ± 0.77 | 0.94 ± 0.20 | 48.92 ± 1.54 | 79.80 ± 4.76 |
| 2. | 8.26 ± 0.75 | 3.49 ± 0.36 | 2.14 ± 0.41 | 0.91 ± 0.03 | 2.19 ± 0.41 | 1.53 ± 0.10 | 3.21 ± 0.29 | 1.47 ± 0.41 | 30.94 ± 3.40 | 64.20 ± 3.19 |
| 3. | 4.22 ± 0.40 | 2.31 ± 0.24 | 3.37 ± 0.76 | 4.48 ± 1.48 | 4.94 ± 1.39 | 10.12 ± 0.88 | 8.51 ± 1.54 | 2.99 ± 0.96 | 33.15 ± 6.30 | 63.50 ± 6.28 |
| 4. | 19.06 ± 2.37 | 7.08 ± 1.50 | 4.91 ± 1.18 | 3.30 ± 0.79 | 3.65 ± 2.05 | 6.43 ± 1.42 | 5.13 ± 1.00 | 2.78 ± 1.00 | 21.23 ± 1.61 | 43.32 ± 3.45 |
| MICE | | | | | | | | | | |
| 1. | 3.00 ± 1.29 | 1.41 ± 0.72 | 2.47 ± 0.26 | 0.90 ± 0.14 | 2.16 ± 0.28 | 1.21 ± 0.47 | 2.57 ± 1.05 | 0.59 ± 0.30 | 64.85 ± 2.74 | 80.38 ± 1.08 |
| 2. | 7.27 ± 2.41 | 1.51 ± 0.53 | 1.65 ± 0.11 | 1.22 ± 0.25 | 3.40 ± 0.25 | 1.67 ± 0.91 | 3.36 ± 0.98 | 1.28 ± 0.52 | 46.39 ± 3.67 | 73.23 ± 2.06 |
| 3. | 6.60 ± 2.37 | 1.23 ± 0.26 | 7.07 ± 0.82 | 4.36 ± 0.43 | 3.31 ± 0.40 | 5.82 ± 0.60 | 4.32 ± 0.15 | 1.12 ± 0.25 | 48.34 ± 2.36 | 70.99 ± 1.94 |
| 4. | 14.66 ± 3.33 | 5.55 ± 1.22 | 2.57 ± 0.47 | 1.02 ± 0.30 | 2.71 ± 0.20 | 3.12 ± 0.85 | 2.57 ± 0.30 | 1.08 ± 0.03 | 35.48 ± 2.92 | 60.15 ± 4.04 |

Scintigraphic Studies on Dogs

Figure 2:
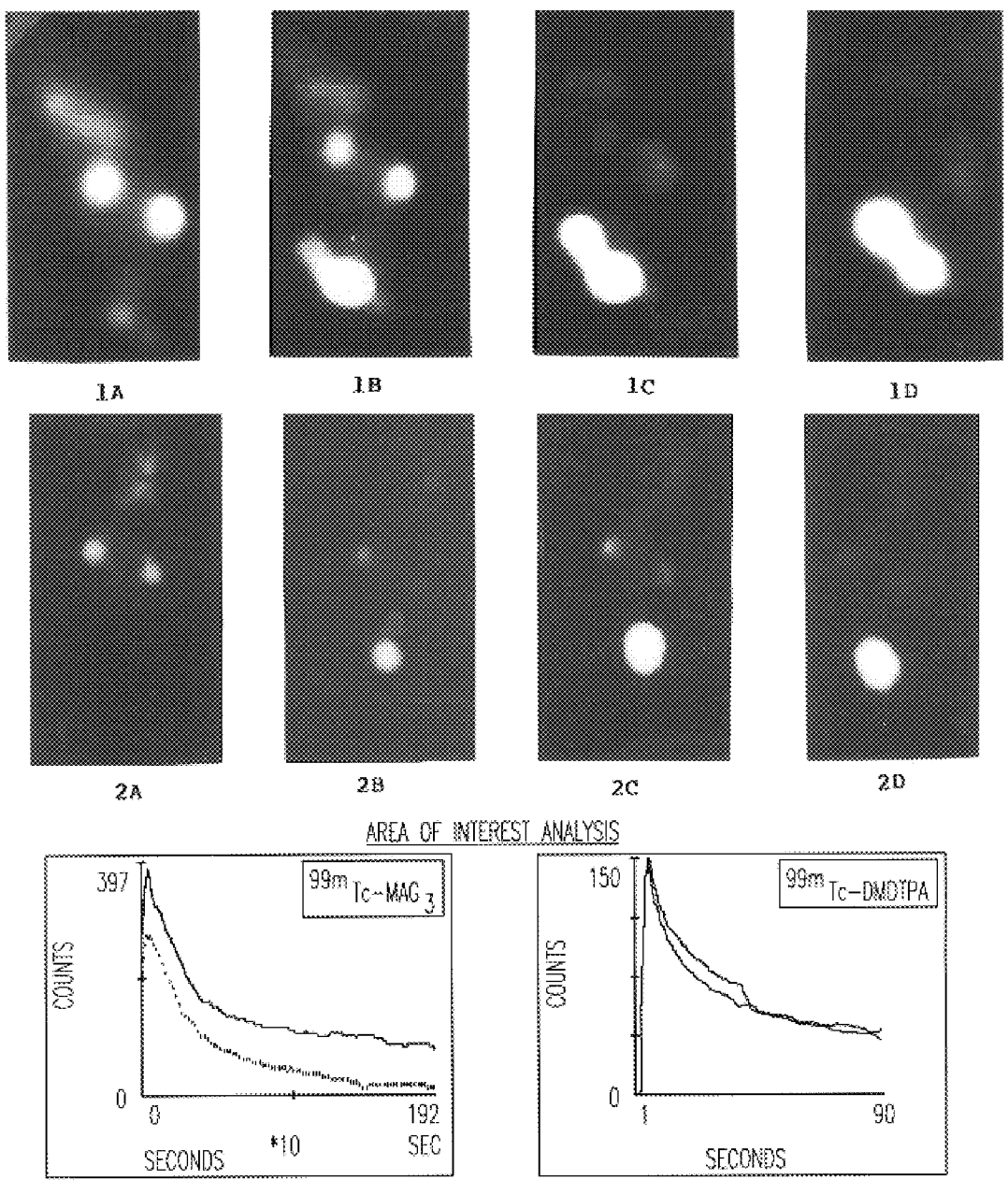

To dogs anaesthetised by pentothal sodium, either of the compounds were introduced via femoral vein while the animal was placed under the collnpterised gamma-camera. Serial images were recorded using appropriate window on a computer tape. The time activity curve was generated from the above frames by placing the area of interest around kidney. The area of interest curves are shown in FIG. 1 and FIG. 2 indicating a comparable clearance of radioactivity from kidney for the above two radiopharmaceuticals.

From the biodistribution in rats or mice or from the scintigraphic experiments on dog it appears that technetium-99m diethylene triamine pentaacetic acid diester is a superior renal function agent than currently available (only in western countries) technetium-99m mercaptoacetylglycylglycylglycine, since there is no hepatobiliary accumulation of technetium-99m diethylene triamine pentaacetic acid diester whereas appreciable amount of technetium-99m mercaptoacetylglycylglycylglycine accumulate in those organs. Moreover, diester of diethylene triamine pentaacetic acid could be easily synthesised com- (a) Adding stannous ion to a dilute aqueous solution of diethylene triamine pentaacetic acid diester;

(b) Keeping the resultant solution obtained in step (a) in an evacuated rubber sealed injection vial flushed with nitrogen;

(c) lyophilizing the said kit and storing the lyophilized product as obtained in step (b) at 4° C.;

(d) radiolabelling the said lyophilized product obtained with Tc-99m by allowing the kit to attain the room temperature before addition of 99m TcO$_4$;

(e) shaking the kit vigorously to obtain the radiolabelled product available for use within a period of one hour.

2. A process as claimed in claim 1 wherein diethylene triamine pentaacetic acid diester used is prepared by

[a] esterifying dianhydride of diethylene triarmine pentaacetic acid, by known methods,

[b] evaporating the resulting semi-solid mass,

[c] tritrating with an organic solvent to get the crude diester, and

[d] preparing the crude diester by recrystallization from alcohol.

3. A process as claimed in claim 2 wherein the esterification is effected by heating dianhydride of diethylene triamine pentaacetic acid with an alcohol in the presence of a solvent.

4. A process as claimed in claim 2 wherein the alcohol used is selected from methanol, ethanol, propanol, and isopropanol.

5. A process as claimed in claim 2 wherein the solvent used is selected from pyridine, piperidine, and picoline.

6. A process as claimed in claim 2 wherein the solvent used for titration is selected from petroleum ether, benzene, and toluene.

7. A process as claimed in claim 2 wherein the alcohol used for crystallization is selected from methanol, ethanol, propanol, and isopropanol.

8. A technetium-99m radiolabeled diethylene triamine pentaacetic acid diester kit prepared by the process of claim 1.

9. A technetium-99m radiolabeled diethylene triamine pentaacetic acid diester kit prepared by the process of claim 2.

10. A technetium-99m radiolabeled diethylene triamine pentaacetic acid diester kit prepared by the process of claim 3.

11. A process for the preparation of a technician-99m radiolabeled diethylene triamine pentaacetic acid dimethylester kit for the diagnosis of renal disorders which comprises (a) Adding stannous ion to a dilute aqueous solution of diethylene triamine pentaacetic acid dimethylester;

(b) Keeping the resultant solution obtained in step (a) in an evacuated rubber sealed injection vial flushed with nitrogen;

(c) Lyophilizing the said kit and storing the lyophilized product as obtained in step (b) at 4° C.;

(d) radiolabelling the said lyophilized product obtained with Tc-99m by allowing the kit to attain room temperature before addition of 99m TcO$_4$; and (e) shaking the kit vigorously to obtain the radiolabeled product available for use within a period of one hour.

12. A process as claimed in claim 11 wherein diethelyne triamine pentaacetic acid dimethylester used is prepared by

[a] esterifying dianhydride of diethylene triamine pentaacetic acid,

[b] evaporating the resulting semi-solid mass,

[c] titrating with an organic solvent to get the crude dimethylester, and

[d] preparing the crude dimethylester by recrystallization from alcohol.

13. A process as claimed in claim 12 wherein the esterification is effected by heating dianhydride of diethylene triamine pentaacetic acid with an alcohol in the presence of a solvent.

14. A process as claimed in claim 12 wherein the alcohol used is selected from methanol, ethanol, propanol, and isopropanol.

15. A process as claimed in claim 12 wherein the solvent is selected from pyridine, piperidine, and picoline.

16. A process as claimed in claim 12 wherein the solvent used for titration is selected from petroleum ether, benzene, and toluene.

17. A process as claimed in claim 12 wherein the alcohol used for crystallization is selected from methanol, ethanol, propanol, and isopropanol.

18. A technetium-99m radiolabeled diethylene triamine pentaacetic acid dimethylester kit prepared by the process of claim 11.

19. A technetium-99m radiolabeled diethylene triamine pentaacetic acid dimethylester kit prepared by the process of claim 12.

20. A technetium-99m radiolabeled diethylene triamine pentaacetic acid dimethylester kit prepared by the process of claim 13.

21. A process for the preparation of a technetium-99m radiolabeled diethylene triamine pentaacetic acid dimethylester or lower alkyl C1–C6 alkyl ester kit for the diagnosis of renal disorders which comprises:

(a) Adding stannous ion to a dilute aqueous solution of diethylene triamine pentaacetic acid dimethylester;

(b) Keeping the resultant solution obtained in step (a) in an evacuated rubber sealed injection vial flushed with nitrogen;

(c) lyophilizing the said kit and storing the lypholized product as obtained in step (b) at 4°;

(d) radiolabelling the said lyphoilized product obtained with Tc-99m by allowing the kit to attain room temperature before addition of 99m TcO$_4$; and (e) shaking the kit vigorously to obtain the radiolabeled product available for use within a period of one hour.

22. A technetium-99m radiolabeled diethylene radiolabeled diethylene triamine pentaacetic acid dimethylester or lower alkyl C1–C6 alkyl ester kit prepared by the process of claim 21.

* * * * *